United States Patent
Joyce et al.

(10) Patent No.: US 12,357,313 B2
(45) Date of Patent: Jul. 15, 2025

(54) CUT OPTIMIZATION FOR EXCESSIVE TISSUE CONDITIONS

(71) Applicant: Covidien LP, Mansfield, MA (US)

(72) Inventors: Steven H. Joyce, Durham, CT (US); David E. Valentine, Hamden, CT (US); Patrick Mozdzierz, Glastonbury, CT (US); Charles R. Kollar, Washington, DC (US); Haley Strassner, New Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/585,215

(22) Filed: Feb. 23, 2024

(65) Prior Publication Data

US 2024/0188960 A1  Jun. 13, 2024

Related U.S. Application Data

(63) Continuation of application No. 17/120,659, filed on Dec. 14, 2020, now Pat. No. 11,911,038.

(60) Provisional application No. 62/960,202, filed on Jan. 13, 2020.

(51) Int. Cl.
   *A61B 17/115*  (2006.01)
   *A61B 17/068*  (2006.01)
   *A61B 17/32*   (2006.01)

(52) U.S. Cl.
   CPC .......... *A61B 17/1155* (2013.01); *A61B 17/32* (2013.01)

(58) Field of Classification Search
   CPC .. A61B 17/068; A61B 17/115; A61B 17/1155
   See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Gloria R Weeks

(57) ABSTRACT

A method of operating a surgical stapler includes advancing a knife assembly at a first velocity until a predetermined force is detected, advancing the knife assembly at a second velocity when the predetermined force is detected, the second velocity being less than the first velocity, and continuing to advance the knife assembly at the second velocity until the knife assembly travels a cutting stroke distance.

17 Claims, 3 Drawing Sheets

(56) References Cited

U.S. PATENT DOCUMENTS

| | | |
|---|---|---|
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |

(56) References Cited

U.S. PATENT DOCUMENTS

| | | | |
|---|---|---|---|
| 6,450,390 | B2 | 9/2002 | Heck et al. |
| 6,478,210 | B2 | 11/2002 | Adams et al. |
| 6,488,197 | B1 | 12/2002 | Whitman |
| 6,491,201 | B1 | 12/2002 | Whitman |
| 6,494,877 | B2 | 12/2002 | Odell et al. |
| 6,503,259 | B2 | 1/2003 | Huxel et al. |
| 6,517,566 | B1 | 2/2003 | Hovland et al. |
| 6,520,398 | B2 | 2/2003 | Nicolo |
| 6,533,157 | B1 | 3/2003 | Whitman |
| 6,551,334 | B2 | 4/2003 | Blatter et al. |
| 6,578,751 | B2 | 6/2003 | Hartwick |
| 6,585,144 | B2 | 7/2003 | Adams et al. |
| 6,588,643 | B2 | 7/2003 | Bolduc et al. |
| 6,592,596 | B1 | 7/2003 | Geitz |
| 6,601,749 | B2 | 8/2003 | Sullivan et al. |
| 6,605,078 | B2 | 8/2003 | Adams |
| 6,605,098 | B2 | 8/2003 | Nobis et al. |
| 6,626,921 | B2 | 9/2003 | Blatter et al. |
| 6,629,630 | B2 | 10/2003 | Adams |
| 6,631,837 | B1 | 10/2003 | Heck |
| 6,632,227 | B2 | 10/2003 | Adams |
| 6,632,237 | B2 | 10/2003 | Ben-David et al. |
| 6,652,542 | B2 | 11/2003 | Blatter et al. |
| 6,659,327 | B2 | 12/2003 | Heck et al. |
| 6,676,671 | B2 | 1/2004 | Robertson et al. |
| 6,681,979 | B2 | 1/2004 | Whitman |
| 6,685,079 | B2 | 2/2004 | Sharma et al. |
| 6,695,198 | B2 | 2/2004 | Adams et al. |
| 6,695,199 | B2 | 2/2004 | Whitman |
| 6,698,643 | B2 | 3/2004 | Whitman |
| 6,716,222 | B2 | 4/2004 | McAlister et al. |
| 6,716,233 | B1 | 4/2004 | Whitman |
| 6,726,697 | B2 | 4/2004 | Nicholas et al. |
| 6,742,692 | B2 | 6/2004 | Hartwick |
| 6,743,244 | B2 | 6/2004 | Blatter et al. |
| 6,763,993 | B2 | 7/2004 | Bolduc et al. |
| 6,769,590 | B2 | 8/2004 | Vresh et al. |
| 6,769,594 | B2 | 8/2004 | Orban, III |
| 6,820,791 | B2 | 11/2004 | Adams |
| 6,821,282 | B2 | 11/2004 | Perry et al. |
| 6,827,246 | B2 | 12/2004 | Sullivan et al. |
| 6,840,423 | B2 | 1/2005 | Adams et al. |
| 6,843,403 | B2 | 1/2005 | Whitman |
| 6,846,308 | B2 | 1/2005 | Whitman et al. |
| 6,852,122 | B2 | 2/2005 | Rush |
| 6,866,178 | B2 | 3/2005 | Adams et al. |
| 6,872,214 | B2 | 3/2005 | Sonnenschein et al. |
| 6,874,669 | B2 | 4/2005 | Adams et al. |
| 6,884,250 | B2 | 4/2005 | Monassevitch et al. |
| 6,905,504 | B1 | 6/2005 | Vargas |
| 6,938,814 | B2 | 9/2005 | Sharma et al. |
| 6,942,675 | B1 | 9/2005 | Vargas |
| 6,945,444 | B2 | 9/2005 | Gresham et al. |
| 6,953,138 | B1 | 10/2005 | Dworak et al. |
| 6,957,758 | B2 | 10/2005 | Aranyi |
| 6,959,851 | B2 | 11/2005 | Heinrich |
| 6,978,922 | B2 | 12/2005 | Bilotti et al. |
| 6,981,941 | B2 | 1/2006 | Whitman et al. |
| 6,981,979 | B2 | 1/2006 | Nicolo |
| 7,032,798 | B2 | 4/2006 | Whitman et al. |
| 7,059,331 | B2 | 6/2006 | Adams et al. |
| 7,059,510 | B2 | 6/2006 | Orban, III |
| 7,077,856 | B2 | 7/2006 | Whitman |
| 7,080,769 | B2 | 7/2006 | Vresh et al. |
| 7,086,267 | B2 | 8/2006 | Dworak et al. |
| 7,114,642 | B2 | 10/2006 | Whitman |
| 7,118,528 | B1 | 10/2006 | Piskun |
| 7,122,044 | B2 | 10/2006 | Bolduc et al. |
| 7,128,748 | B2 | 10/2006 | Mooradian et al. |
| 7,141,055 | B2 | 11/2006 | Abrams et al. |
| 7,168,604 | B2 | 1/2007 | Milliman et al. |
| 7,179,267 | B2 | 2/2007 | Nolan et al. |
| 7,182,239 | B1 | 2/2007 | Myers |
| 7,195,142 | B2 | 3/2007 | Orban, III |
| 7,207,168 | B2 | 4/2007 | Doepker et al. |
| 7,220,237 | B2 | 5/2007 | Gannoe et al. |
| 7,234,624 | B2 | 6/2007 | Gresham et al. |
| 7,235,089 | B1 | 6/2007 | McGuckin, Jr. |
| RE39,841 | E | 9/2007 | Bilotti et al. |
| 7,285,125 | B2 | 10/2007 | Viola |
| 7,303,106 | B2 | 12/2007 | Milliman et al. |
| 7,303,107 | B2 | 12/2007 | Milliman et al. |
| 7,309,341 | B2 | 12/2007 | Ortiz et al. |
| 7,322,994 | B2 | 1/2008 | Nicholas et al. |
| 7,325,713 | B2 | 2/2008 | Aranyi |
| 7,334,718 | B2 | 2/2008 | McAlister et al. |
| 7,335,212 | B2 | 2/2008 | Edoga et al. |
| 7,364,060 | B2 | 4/2008 | Milliman |
| 7,398,908 | B2 | 7/2008 | Holsten et al. |
| 7,399,305 | B2 | 7/2008 | Csiky et al. |
| 7,401,721 | B2 | 7/2008 | Holsten et al. |
| 7,401,722 | B2 | 7/2008 | Hur |
| 7,407,075 | B2 | 8/2008 | Holsten et al. |
| 7,410,086 | B2 | 8/2008 | Ortiz et al. |
| 7,422,136 | B1 | 9/2008 | Marczyk |
| 7,422,137 | B2 | 9/2008 | Manzo |
| 7,422,138 | B2 | 9/2008 | Bilotti et al. |
| 7,431,191 | B2 | 10/2008 | Milliman |
| 7,438,718 | B2 | 10/2008 | Milliman et al. |
| 7,455,676 | B2 | 11/2008 | Holsten et al. |
| 7,455,682 | B2 | 11/2008 | Viola |
| 7,481,347 | B2 | 1/2009 | Roy |
| 7,494,038 | B2 | 2/2009 | Milliman |
| 7,506,791 | B2 | 3/2009 | Omaits et al. |
| 7,516,877 | B2 | 4/2009 | Aranyi |
| 7,527,185 | B2 | 5/2009 | Harari et al. |
| 7,537,602 | B2 | 5/2009 | Whitman |
| 7,540,839 | B2 | 6/2009 | Butler et al. |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,556,186 | B2 | 7/2009 | Milliman |
| 7,559,451 | B2 | 7/2009 | Sharma et al. |
| 7,585,306 | B2 | 9/2009 | Abbott et al. |
| 7,588,174 | B2 | 9/2009 | Holsten et al. |
| 7,600,663 | B2 | 10/2009 | Green |
| 7,611,038 | B2 | 11/2009 | Racenet et al. |
| 7,635,385 | B2 | 12/2009 | Milliman et al. |
| 7,669,747 | B2 | 3/2010 | Weisenburgh, II et al. |
| 7,686,201 | B2 | 3/2010 | Csiky |
| 7,694,864 | B2 | 4/2010 | Okada et al. |
| 7,699,204 | B2 | 4/2010 | Viola |
| 7,708,181 | B2 | 5/2010 | Cole et al. |
| 7,717,313 | B2 | 5/2010 | Criscuolo et al. |
| 7,721,932 | B2 | 5/2010 | Cole et al. |
| 7,726,539 | B2 | 6/2010 | Holsten et al. |
| 7,743,958 | B2 | 6/2010 | Orban, III |
| 7,744,627 | B2 | 6/2010 | Orban, III et al. |
| 7,770,776 | B2 | 8/2010 | Chen et al. |
| 7,771,440 | B2 | 8/2010 | Ortiz et al. |
| 7,776,060 | B2 | 8/2010 | Mooradian et al. |
| 7,793,813 | B2 | 9/2010 | Bettuchi |
| 7,802,712 | B2 | 9/2010 | Milliman et al. |
| 7,823,592 | B2 | 11/2010 | Bettuchi et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,845,536 | B2 | 12/2010 | Viola et al. |
| 7,845,538 | B2 | 12/2010 | Whitman |
| 7,857,187 | B2 | 12/2010 | Milliman |
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,012,170 B2 | 9/2011 | Whitman et al. |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,801 B2 | 10/2012 | Zemlok et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,994 B2 | 1/2014 | Zemlok et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,237,921 B2 | 1/2016 | Messerly et al. |
| 10,000,065 B1 | 6/2018 | Baker et al. |
| 10,201,365 B2 | 2/2019 | Boudreaux et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |

(56) References Cited

U.S. PATENT DOCUMENTS

| | | |
|---|---|---|
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 11,045,199 B2 | 6/2021 | Mozdzierz et al. |
| 11,109,866 B2* | 9/2021 | Shelton, IV ............ H01Q 1/22 |
| 11,596,400 B2 | 3/2023 | Mozdzierz et al. |
| 11,911,038 B2 | 2/2024 | Joyce et al. |
| 2003/0111507 A1 | 6/2003 | Nunez |
| 2004/0092992 A1 | 5/2004 | Adams et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0245841 A1 | 10/2008 | Smith et al. |
| 2008/0251568 A1 | 10/2008 | Zemlok et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0069942 A1 | 3/2010 | Shelton, IV |
| 2010/0084453 A1 | 4/2010 | Hu |
| 2010/0096431 A1 | 4/2010 | Smith et al. |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0270355 A1 | 10/2010 | Whitman et al. |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0139851 A1 | 6/2011 | McCuen |
| 2011/0144640 A1 | 6/2011 | Heinrich et al. |
| 2011/0155781 A1 | 6/2011 | Swensgard et al. |
| 2011/0192882 A1 | 8/2011 | Hess et al. |
| 2011/0204119 A1 | 8/2011 | McCuen |
| 2011/0270355 A1 | 11/2011 | Chambers |
| 2011/0288573 A1 | 11/2011 | Yates et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0046352 A1 | 2/2014 | Reboa et al. |
| 2014/0158747 A1 | 6/2014 | Measamer et al. |
| 2014/0246474 A1 | 9/2014 | Hall et al. |
| 2014/0284370 A1 | 9/2014 | Sahin |
| 2015/0053749 A1 | 2/2015 | Shelton, IV et al. |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2016/0066916 A1 | 3/2016 | Overmyer et al. |
| 2016/0143641 A1 | 5/2016 | Sapienza et al. |
| 2016/0157856 A1 | 6/2016 | Williams et al. |
| 2016/0302792 A1 | 10/2016 | Motai |
| 2017/0128068 A1 | 5/2017 | Zhang et al. |
| 2017/0296185 A1 | 10/2017 | Swensgard et al. |
| 2017/0333033 A1 | 11/2017 | Valentine et al. |
| 2018/0353186 A1 | 12/2018 | Mozdzierz et al. |
| 2018/0360446 A1 | 12/2018 | Shelton, IV et al. |
| 2019/0099180 A1 | 4/2019 | Leimbach et al. |
| 2019/0200998 A1 | 7/2019 | Shelton, IV et al. |
| 2019/0201034 A1 | 7/2019 | Shelton, IV et al. |
| 2019/0314015 A1 | 10/2019 | Shelton, IV et al. |
| 2020/0155149 A1 | 5/2020 | Calderoni et al. |
| 2020/0405304 A1 | 12/2020 | Mozdzierz et al. |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3231373 A2 | 10/2017 |
| EP | 3417804 A1 | 12/2018 |
| EP | 3420972 A1 | 1/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |

(56) References Cited

FOREIGN PATENT DOCUMENTS

| | | | |
|---|---|---|---|
| WO | 8706448 | A1 | 11/1987 |
| WO | 8900406 | A1 | 1/1989 |
| WO | 9006085 | A1 | 6/1990 |
| WO | 9835614 | A1 | 8/1998 |
| WO | 0154594 | A1 | 8/2001 |
| WO | 02080781 | A2 | 10/2002 |
| WO | 2008107918 | A1 | 9/2008 |

OTHER PUBLICATIONS

European Examination Report from Appl. No. 14181908.6 dated May 3, 2016.
European Search Report dated Mar. 17, 2021, corresponding to counterpart European Application 21151140.7; 9 pages.

* cited by examiner

CUT OPTIMIZATION FOR EXCESSIVE TISSUE CONDITIONS

CROSS-REFERENCE TO RELATED APPLICATIONS

This application is a continuation of U.S. patent application Ser. No. 17/120,659 filed on Dec. 14, 2020, now U.S. Pat. No. 11,911,038, which claims the benefit of and priority to U.S. Provisional Patent Application Ser. No. 62/960,202 filed on Jan. 13, 2020, the entire disclosures of which are incorporated by reference herein.

FIELD

The disclosure is directed to powered circular stapling devices and, more particularly, to optimizing the cutting stroke of powered circular stapling devices.

BACKGROUND

Conventional powered circular stapling devices typically include a one-time use circular reload releasably secured to a reusable adapter and/or a handle assembly. During a stapling procedure, two layers of tissue are clamped between the circular reload and an anvil assembly that is attached to a trocar of the adapter assembly. After the tissue is clamped between the circular reload and the anvil assembly to define a specific tissue gap between the circular reload and the anvil assembly, the handle assembly can be actuated to drive a staple pusher within the circular reload and advance staples through the tissue into staple pockets on the anvil assembly.

Subsequent to staple formation, the handle assembly can be actuated to drive a knife pusher within the circular reload at a steady speed to advance an annular knife from within the circular reload. As the annular knife is advanced, the annular knife engages and cuts a hole in the clamped and stapled tissue to form an anastomosis. The knife pusher is then retracted, returning the annular knife back into the circular reload to prevent exposure of the annular knife. The knife pusher may retract the annular knife beyond its initial position to, for example, engage detents which retain the annular knife within the circular reload.

Prior to advancing the knife pusher, a large amount of tissue may be captured within the circular reload and/or between the circular reload and the anvil assembly. Current software controls the annular knife by moving the knife pusher at a constant speed until a specified cut force limit, e.g., 275 lbf, is detected by a strain gage supported inside the handle assembly or adapter assembly. Excessive amounts of tissue inside the circular reload and/or between the circular reload and the anvil assembly during advancement of the knife assembly may raise the amount of pressure against the knife pusher assembly such that the cut force limit is reached prior to the annular knife completely cutting through the tissue. This may result in an incomplete cut.

Therefore, it would be beneficial to have a powered circular stapling device with an optimized cutting stroke for accommodating a large amount of tissue inside the circular reload.

SUMMARY

A method of operating a surgical stapler is provided. The method includes advancing a knife assembly at a first velocity until a predetermined force on the knife assembly is detected, advancing the knife assembly at a second velocity when the predetermined force is detected, the second velocity being less than the first velocity, and continuing to advance the knife assembly at the second velocity until the knife assembly travels a cutting stroke distance.

In embodiments, the first velocity is from about 3.5 in/min to about 4.0 in/min. The second velocity may be from about 0.25 in/min to about 0.5 in/min. The predetermined force may be about 275 lbf. The cutting stroke distance may be from about 0.20 in. to about 0.350 in. The cutting stroke distance may be about 0.325 in.

Another method of operating a surgical stapler is provided including advancing a knife assembly at a first velocity until a predetermined force on the knife assembly is detected, advancing the knife assembly at a second velocity when the predetermined force is detected, the second velocity being less than the first velocity, continuing to advance the knife assembly at the second velocity until a second predetermined force on the knife assembly is detected, and advancing the knife assembly at a third velocity until the knife assembly travels a cutting stroke distance.

In embodiments, the first velocity is from about 3.5 in/min to about 4.0 in/min. The second velocity may be from about 0.25 in/min to about 0.5 in/min. The predetermined force may be about 275 lbf. The cutting stroke distance may be from about 0.20 in. to about 0.350 in. The cutting stroke distance may be about 0.325 in.

BRIEF DESCRIPTION OF THE DRAWINGS

Various aspects of the disclosed circular reload are described herein below with reference to the drawings, wherein.

DETAILED DESCRIPTION

Figure 1:
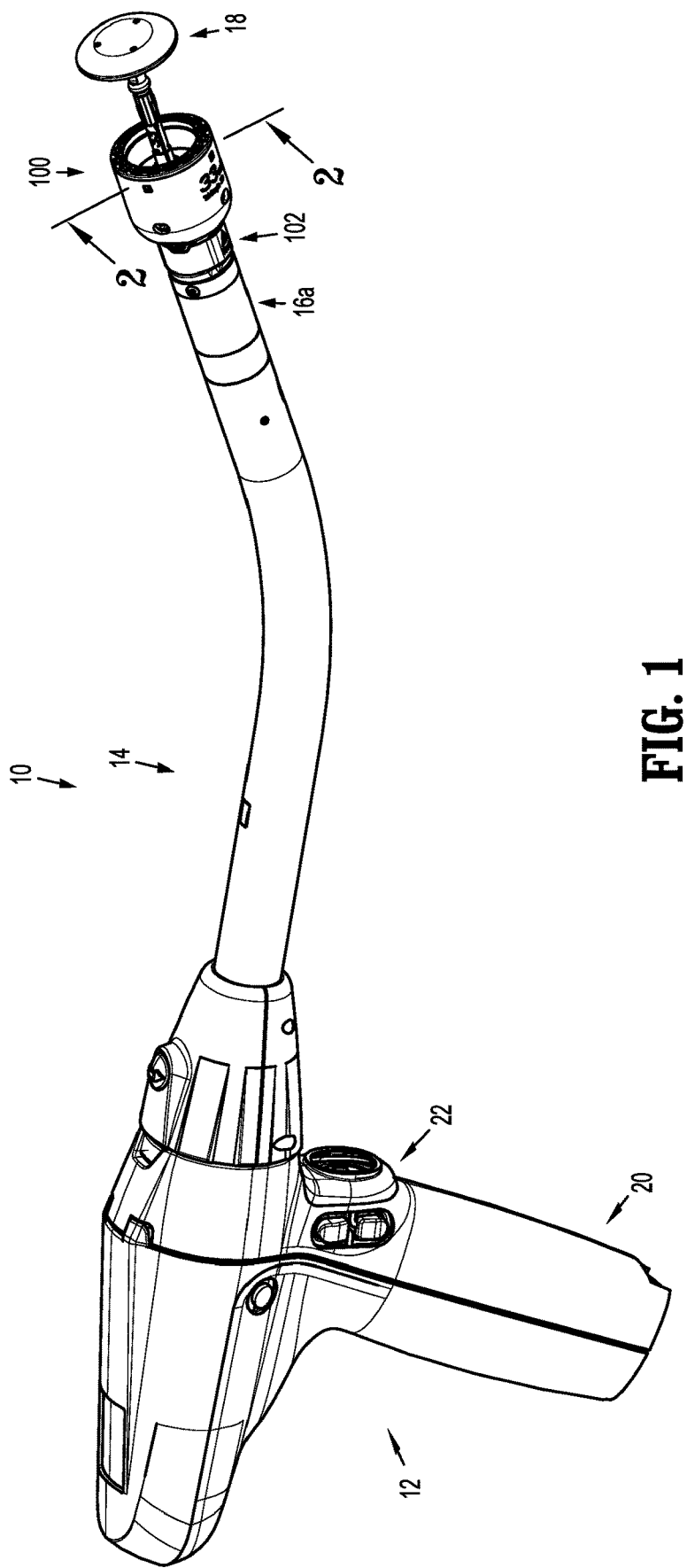
FIG. 1 is a side perspective view of a circular stapling device including exemplary aspects of the disclosed circular reload in accordance with the disclosure.

The disclosed circular reload will now be described in detail with reference to the drawings in which like reference numerals designate identical or corresponding elements in each of the several views. However, it is to be understood that the aspects of the disclosure provided herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Figure 2:
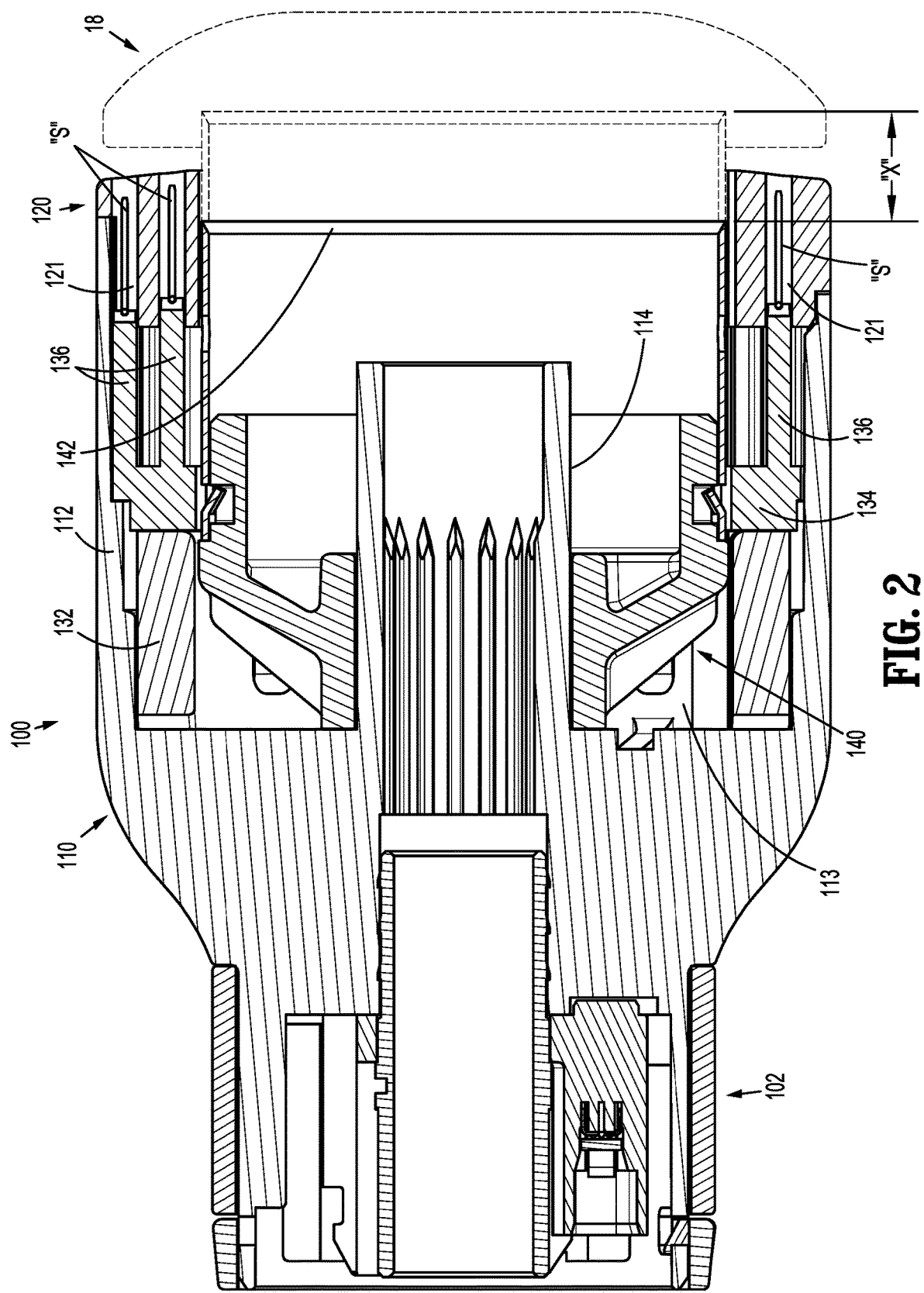
FIG. 2 is a side perspective view of the circular reload of FIG. 1.

FIGS. 1 and 2 illustrate a circular stapling device 10 including an exemplary circular reload shown generally as circular reload 100. The stapling device 10 includes a handle assembly 12, an elongate body or adaptor assembly 14, the circular reload 100, and an anvil assembly 18 that is supported for movement in relation to the circular reload 100 between spaced and approximated or clamped positions as is known in the art. The circular reload 100 includes a proximal portion 102 that is releasably coupled to a distal portion 16a of the elongate body 16. The handle assembly 12 includes a stationary grip 20 that supports actuation buttons 22 for controlling operation of various functions of the stapling device 10 including approximation of the circular reload 100 and anvil assembly 18, firing of staples from the circular reload 100, and cutting or coring of tissue (not shown) clamped between the circular reload 100 and the anvil assembly 18.

The stapling device 10 is illustrated as an electrically powered stapling device including an electrically powered handle assembly 12 that may support one or more batteries (not shown). The elongate body 14 is in the form of an adaptor assembly 14 that translates power from the handle assembly 12 to the circular reload 100 and anvil assembly 18. Examples of electrically powered stapling devices can be found in U.S. Pat. Nos. 9,055,943, 9,023,014, and U.S. Publication Nos. 2018/0125495 ("the '495 Publication"), and 2017/0340351.

FIG. 2 illustrates the circular reload 100 which includes a shell housing 110, a staple cartridge 120 supporting a plurality of staples "S", a staple pusher assembly 130, and a knife pusher assembly 140 that supports an annular knife 132. The staple cartridge 120 is annular and defines annular rows of staple pockets 121. Each of the staple pockets 121 supports one of the plurality of staples "S". The circular reload 100 will only be described in detail to the extent necessary to fully disclose the novel aspects of the disclosure. For a detailed description of an exemplary circular reload, please refer to the '495 Publication.

Briefly, the staple pusher assembly 130 of the circular reload 100 includes a staple pushing member 132 and an annular pusher 134. The annular pusher 134 of the circular reload 100 has a plurality of fingers 136. Each of the plurality of fingers 136 is received within a respective one of the staple pockets 121 of the staple cartridge 120 and is movable through the respective staple pocket 121 to eject the staples "S" from the staple pockets 121 when the staple pushing member 132 is moved from a retracted position to an advanced position within the shell housing 110.

The shell housing 110 of the circular reload 100 includes an outer housing portion 112 and an inner housing portion 114 spaced from the outer housing portion 112 to define an annular cavity 113. The pusher assembly 130 is movable within the annular cavity 113 between a retracted position (FIG. 2) and an advanced position (not shown) independently of the knife pusher assembly 140 to eject the staples "S" from the staple cartridge 120. The knife pusher assembly 140, including the annular knife 142, is movable from a retracted position (FIG. 2) to an advanced position (shown in phantom) to cut the tissue (not shown).

The distance between the position of the annular knife 142 when the knife pusher assembly 140 is in the retracted position and the position of the annular knife 142 when the knife pusher assembly 140 is in the advanced position is indicated in FIG. 2 as a cutting stroke distance "X". In embodiments, the cutting stroke distance "X" is from about 0.20 inches to about 0.35 inches. In certain embodiments, the cutting stroke distance "X" is about 0.325 inches. To ensure that the tissue (not shown) clamped between the circular reload 100 and the anvil assembly 18 is completely cut during a stapling procedure, it is necessary for the annular knife 142 to travel the entire cutting stroke distance "X".

To prevent damage to the components of the circular stapling device 10 during a stapling procedure, the force applied to knife pusher assembly 140 is typically limited to a predetermined force. For example, in certain aspects of the disclosure, the cut force limit is 275 lbf. However, during the stapling procedure, an excessive amount of tissue (not shown) may become trapped within the circular reload 100 and/or between the circular reload 100 and the anvil assembly 18 and may cause the cut force limit of the circular stapling device 10 to be reached before the annular knife 142 travels the entire cutting stroke distance "X". This may result in an incomplete cut of the tissue.

In order to compensate for excessive amounts of tissue that may be clamped between the circular reload 100 and the anvil assembly 18, software included with the circular stapling device 10 is programmed to reduce a speed of travel, i.e., velocity, of the knife pusher assembly 140, and more particularly, the annular knife 142, when the cut force limit is reached prior to the annular knife 142 travelling through the entire cutting stroke distance "X". The software may also increase the cut force limit. In aspects of the disclosure, the velocity of the annular knife 142 is reduced by 10%. In embodiments, a first or initial velocity of the knife pusher assembly 140 is from about 3.5 in/min to about 4.0 in/min. and a second velocity is from about 0.25 in/min to about 0.5 in/min. Simultaneously, the cut force limit may be increased to, for example, 350 lbf. By reducing the speed at which the annular knife 142 travels, the excess tissue trapped within the circular reload 100 and/or between the circular reload 100 and the anvil assembly 18 is able to relax, i.e., release fluid, and return to a state of equilibrium.

In instances where the initial velocity of the annular knife 142 is reduced to the second velocity and the increased cut force limit is attained before the annular knife 142 travels the entire cutting stroke distance "X", the velocity of the annular knife 142 may be further reduced to a third velocity. The further reduction in velocity may also be accompanied by an increase in the cut force limit. Subsequent reductions in velocity of the annular knife 142 and increases in the cut force limit may occur until the annular knife 142 travels the entire cutting stroke distance "X".

Figure 3:
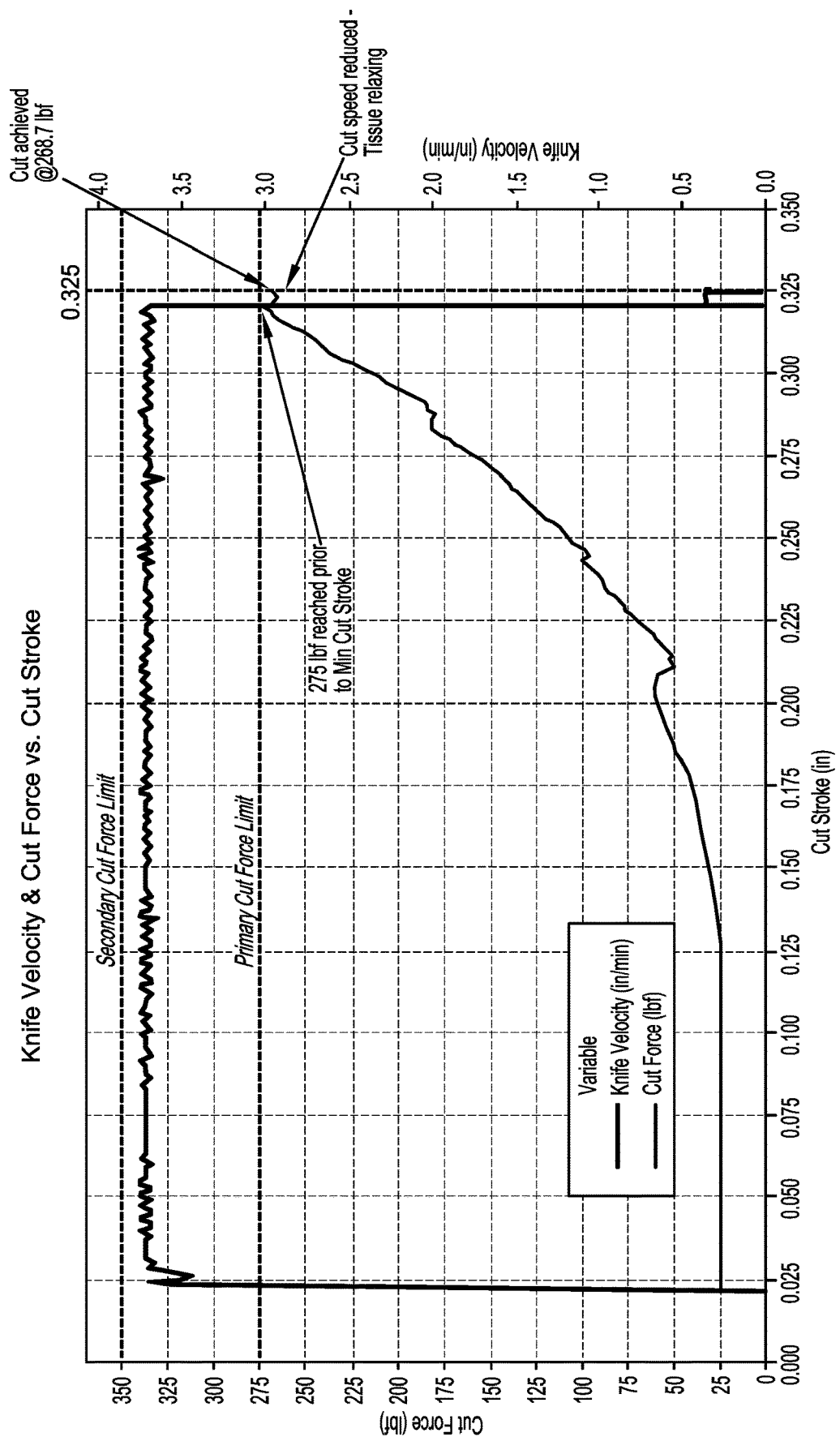
FIG. 3 is a chart plotting knife velocity and cut force relative to cut stroke.

As illustrated in the chart of FIG. 3, by reducing the speed of the annular knife 142 to allow time for the tissue clamped within the circular reload 100 to relax, the cut force required to move the annular knife 142 through the entire cut stroke distance "X" is reduced.

In other aspects of the disclosure, the annular knife 142 may be moved at an initial velocity until the annular knife 142 experiences resistance, i.e., the annular knife 142 engages tissue. The velocity of the annular knife 142 may then be reduced, as described above, until the annular knife 142 travels the entire cutting stroke distance "X". Increasing the velocity of the annular knife 142 prior to the annular knife 142 engaging tissue reduces firing time of the surgical stapling device 10 when the annular knife 142 travels through the circular reload 100.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A powered stapling device comprising:
   a staple cartridge including a plurality of staples and an annular knife movable relative to the staple cartridge;
   an anvil assembly movable relative to the staple cartridge; and
   software configured for:
      advancing the annular knife at a first velocity until a predetermined force on the annular knife is detected;
      increasing force applied by the annular knife above the predetermined force in response to the annular knife reaching a first position;
      determining that the annular knife reached a second position distal of the first position, the second position corresponding to a minimum cutting stroke distance;
      after the minimum cutting stroke distance is achieved, advancing the annular knife at a second velocity when the force above the predetermined force is detected, the second velocity being less than the first velocity; and
      continuing to advance the annular knife at the second velocity until the annular knife reaches a maximum cutting stroke distance.

2. The powered stapling device according to claim 1, wherein the first velocity is from about 3.5 in/min to about 4.0 in/min.

3. The powered stapling device according to claim 1, wherein the second velocity is from about 0.25 in/min to about 0.5 in/min.

4. The powered stapling device according to claim 1, wherein the predetermined force is about 275 lbf.

5. The powered stapling device according to claim 1, wherein the maximum cutting stroke distance is from about 0.20 in. to about 0.350 in.

6. The powered stapling device according to claim 5, wherein the maximum cutting stroke distance is about 0.325 in.

7. The powered stapling device according to claim 1, wherein the predetermined force occurs when the annular knife engages tissue.

8. A powered stapling device comprising:
   a staple cartridge including a plurality of staples and an annular knife movable relative to the staple cartridge;
   an anvil assembly movable relative to the staple cartridge; and
   software configured for:
      advancing the annular knife at a first velocity from a start position to a stop position;
      lowering the first velocity to a second velocity in response to reaching an initial cut force limit prior to the annular knife reaching the stop position; and
      continuing to advance the annular knife at the second velocity until the annular knife reaches the stop position.

9. The powered stapling device according to claim 8, wherein the software is further configured for:
   increasing the cut force limit to a higher cut force limit in response to reaching an initial cut force limit prior to the annular knife reaching the stop position; and
   continuing to advance the annular knife at the second velocity until the annular knife reaches the stop position.

10. The powered stapling device according to claim 9, wherein the software is further configured for:
    lowering the second velocity to a third velocity in response to reaching the higher cut force limit prior to the annular knife reaching the stop position.

11. The powered stapling device according to claim 10, wherein the software is further configured for:
    continuing to advance the annular knife at the third velocity until the annular knife reaches the stop position.

12. The powered stapling device according to claim 8, wherein the first velocity is from about 3.5 in/min to about 4.0 in/min.

13. The powered stapling device according to claim 8, wherein the second velocity is from about 0.25 in/min to about 0.5 in/min.

14. The powered stapling device according to claim 8, wherein the initial cut force limit is about 275 lbf.

15. The powered stapling device according to claim 8, wherein a cutting stroke distance between the starting position and the stop position is from about 0.20 in. to about 0.350 in.

16. The powered stapling device according to claim 15, wherein the cutting stroke distance is about 0.325 in.

17. The powered stapling device according to claim 8, wherein the higher cut force limit is about 350 lbf.

* * * * *